United States Patent
Rella

(10) Patent No.: US 9,606,029 B2
(45) Date of Patent: Mar. 28, 2017

(54) LEAK DISTANCE ESTIMATION METHOD USING CORRELATION MEASUREMENTS AT ISOLATED SPATIAL POINTS IN A PLUME

(71) Applicant: Picarro, Inc., Santa Clara, CA (US)

(72) Inventor: Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 0 days.

(21) Appl. No.: 15/275,434

(22) Filed: Sep. 25, 2016

(65) Prior Publication Data

US 2017/0010175 A1 Jan. 12, 2017

Related U.S. Application Data

(63) Continuation-in-part of application No. 13/866,660, filed on Apr. 19, 2013, now Pat. No. 9,470,517.

(60) Provisional application No. 61/636,300, filed on Apr. 20, 2012.

(51) Int. Cl.
| | |
|---|---|
| *G01P 5/00* | (2006.01) |
| *G01N 31/00* | (2006.01) |
| *G06K 9/00* | (2006.01) |
| *G01N 1/26* | (2006.01) |
| *G01N 21/3504* | (2014.01) |
| *G01N 33/00* | (2006.01) |
| *G01N 1/22* | (2006.01) |
| *G01M 3/20* | (2006.01) |
| *G08B 21/12* | (2006.01) |

(52) U.S. Cl.
CPC ............... *G01N 1/26* (2013.01); *G01M 3/20* (2013.01); *G01N 1/2273* (2013.01); *G01N 21/3504* (2013.01); *G01N 33/0004* (2013.01); *G01N 33/0062* (2013.01); *G08B 21/12* (2013.01)

(58) Field of Classification Search
CPC ...... G08B 21/12; G01N 1/26; G01N 21/3504; G01N 33/0004; G01N 2201/025; G01N 33/0062; G01N 1/2273; G01M 3/20
USPC ............ 702/3, 24, 127, 142; 73/23.2, 23.28; 382/100, 154, 191, 207, 294
See application file for complete search history.

(56) References Cited

U.S. PATENT DOCUMENTS

| | | | | |
|---|---|---|---|---|
| 8,284,986 | B2 * | 10/2012 | Wolowelsky | G01N 21/3518 382/100 |
| 8,510,059 | B2 * | 8/2013 | Prince | G01N 33/0062 702/142 |
| 2011/0213554 | A1 * | 9/2011 | Archibald | G01V 9/007 702/6 |

OTHER PUBLICATIONS

Turner, "Workbook of atmospheric dispersion estimates", 1970, EPA report, pp. 1-91 (reprinted by CRC press in 1994).

(Continued)

*Primary Examiner* — An Do
(74) *Attorney, Agent, or Firm* — Lumen Patent Firm

(57) ABSTRACT

Repeated simultaneous concentration measurements at spatially separated points are used to provide information on the lateral spatial extent of a gas plume. More specifically the spatial correlations in this data provide this information. Fitting a gas plume model directly to this multi-point data can provide good estimates of total plume emission. The distance between the plume source and the measurement points does not need to be known to provide these estimates. It is also not necessary to perform any detailed atmospheric modeling. These estimates of the lateral spatial extent of a gas plume can also be used to provide a distance estimate to the source of the gas plume.

13 Claims, 4 Drawing Sheets

(56) References Cited

OTHER PUBLICATIONS

Gifford "Statistical properties of a fluctuating plume dispersion model", 1959, Advances in geophysics v6 pp. 117-137.
Peterson et al., "Comparison of results from a meandering-plume model with measured atmospheric tracer concentration fluctuations." 1992, Journal of Applied Meteorology v31n6, pp. 553-564.

* cited by examiner

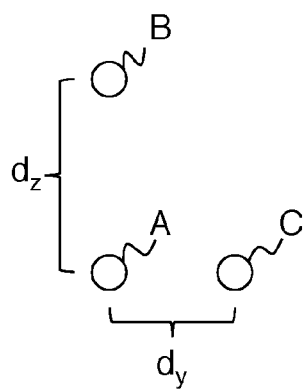
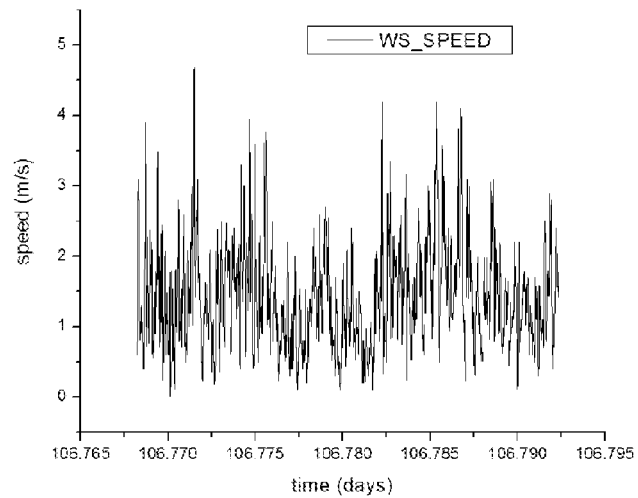
FIG. 3
FIG. 4
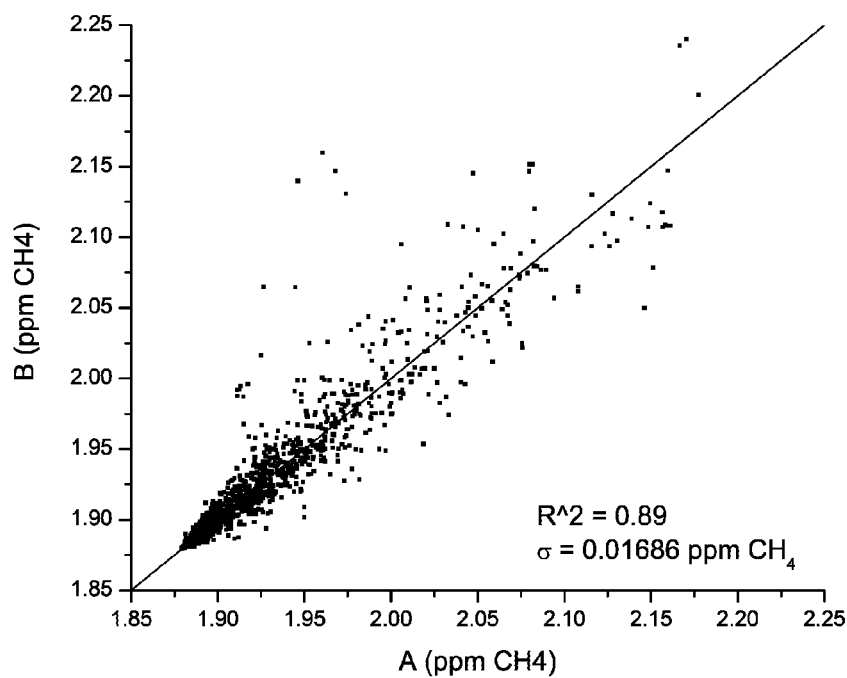
FIG. 5

LEAK DISTANCE ESTIMATION METHOD USING CORRELATION MEASUREMENTS AT ISOLATED SPATIAL POINTS IN A PLUME

CROSS REFERENCE TO RELATED APPLICATIONS

This application is a continuation in part of U.S. Ser. No. 13/866,660, filed Apr. 19, 2013, and hereby incorporated by reference in its entirety.

Application Ser. No. 13/866,660 claims the benefit of U.S. provisional patent application 61/636,300, filed on Apr. 20, 2012, and hereby incorporated by reference in its entirety.

FIELD OF THE INVENTION

This invention relates to gas plume estimation.

BACKGROUND

Gas concentration measurements are often employed to measure and/or monitor emissions into the atmosphere. Typically, a source of emissions will result in an emission plume in the atmosphere, and the main quantity of interest is often the total amount of emission in the plume. A concentration measurement at a single point is not sufficient for this task. Attempts have been made to use multi-point measurements, combined with detailed atmospheric modeling (e.g., including a turbulence model for the atmosphere) to provide plume emission estimates. However, these approaches suffer from undesirable model complexity, and the results are often disappointing in practice.

Another known approach is to take measurements over a long period of time (e.g., tens of minutes). Averaging these measurements can reduce the effect of the stochastic variability of the propagating plume sufficiently such that fitting the results of such data averaging to a simple plume model (e.g., a Gaussian plume model) can provide adequate results in some cases. However, formulating the model for the plume requires detailed knowledge of the atmosphere, and understanding of the atmospheric flow over the neighboring terrain, including obstacles. In addition, one must also know the distance to the leak and the height of the leak above ground. Any errors in the formulation of the model can lead to an unwanted bias in the reported emission rate results.

Another approach is to directly measure the emission rate by physically enclosing the leak with an impermeable surface (such as a chamber or bag), and then measuring the rate of increase of concentration in the enclosed volume. In many cases, a known flow of clean gas is injected into the volume, such that the concentration in the enclosed volume will asymptotically approach a value which is related to the emission rate of the gas, given the injection rate of the clean gas. However, this method requires physical access to the leak (or leaks), is labor intensive, and prone to underestimation bias if not all the leaks in a given facility are identified.

Accordingly, it would be an advance in the art to alleviate these limitations of complex modeling or direct access to the leak.

SUMMARY

The present approach is based on the observation that an emission plume tends to maintain its integrity (i.e., its lateral spatial concentration profile) as it varies in time. In other words, the main time dependence of the plume can be regarded as a meandering of the plume in the background atmosphere. As a result, repeated simultaneous concentration measurements at spatially separated points can provide information on the lateral spatial extent of the plume. For example, consider two vertically separated points A and B. Repeated simultaneous concentration measurements at A and B provide concentration data $C_{Aj}$ and $C_{Bj}$, where j is an index. The spatial correlation of these concentrations (as can be visualized using a scatter plot of $C_{Aj}$ vs. $C_{Bj}$) can be used to estimate the vertical extent of the plume. Similarly, if points A and C are horizontally separated, then the spatial correlation of $C_{Aj}$ vs. $C_{Cj}$ can be used to estimate the horizontal extent of the plume. Once the horizontal and vertical extent of the plume have been estimated, the plume emission can be estimated using a simple plume model (i.e., no plume meandering in the model), and the average wind speed perpendicular to the A-B-C plane. These estimates of the lateral spatial extent of a gas plume can also be used to provide a distance estimate to the source of the gas plume.

BRIEF DESCRIPTION OF THE DRAWINGS

FIG. 3 shows a preferred arrangement of measurement points.

FIG. 4 shows an example of measured wind speed.

FIG. 5 shows an exemplary correlation plot for two independent measurements at the same point.

DETAILED DESCRIPTION

Figure 1:
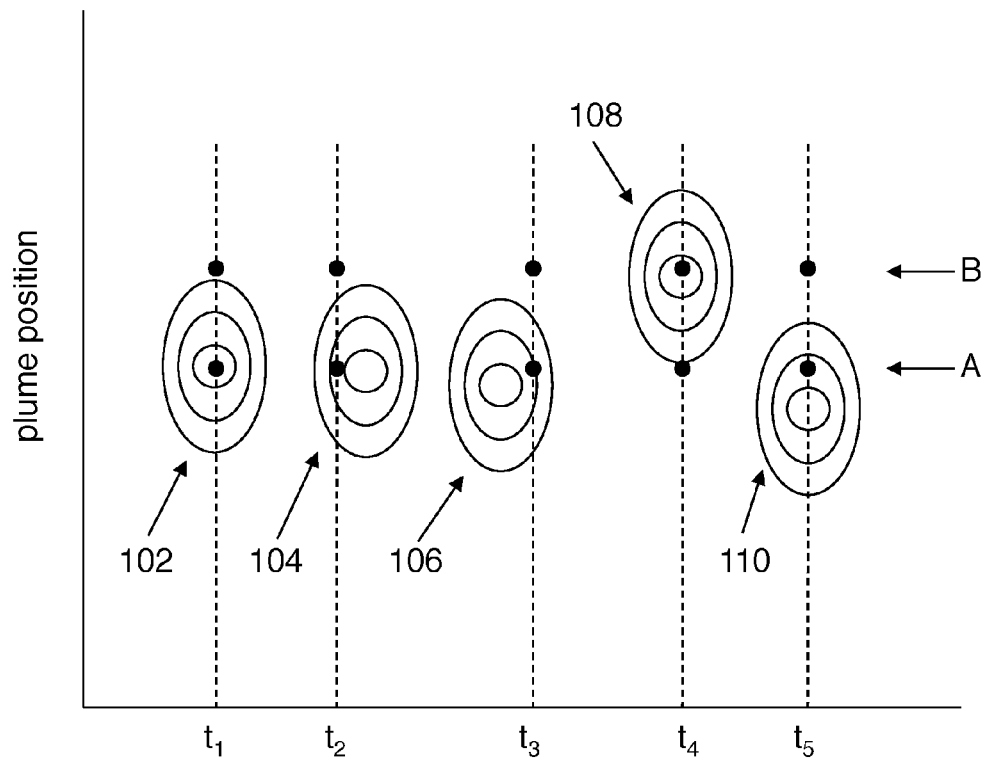
FIG. 1 shows examples of several plume locations relative to two fixed measurement points.

As indicated above, the present approach is based on the assumption that the time dependence of measured concentration from an emission plume is mainly due to meandering of the plume within the atmosphere. FIG. 1 shows examples of several plume locations relative to two fixed measurement points A and B that are vertically separated. At time $t_1$, the plume location is shown by 102. Similarly, at times $t_2$, $t_3$, $t_4$, and $t_5$, the plume locations are shown by 104, 106, 108, and 110 respectively.

Figure 2:
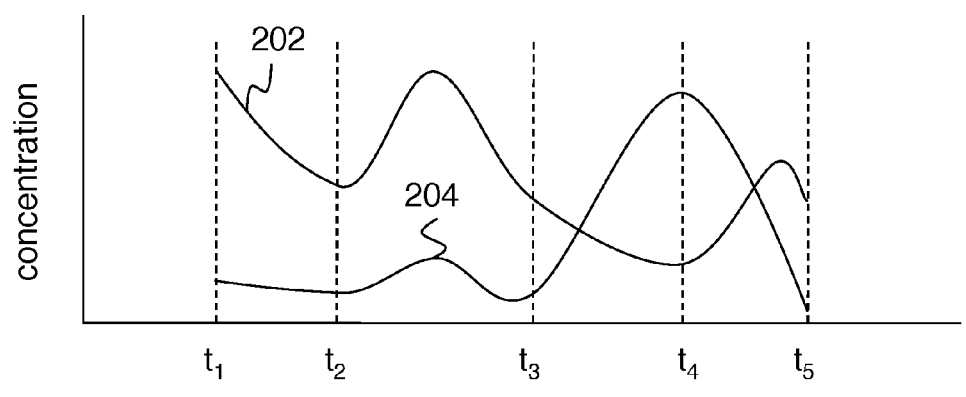
FIG. 2 schematically shows concentration measurements to be expected at the measurement points for the example of FIG. 1.

FIG. 2 schematically shows concentration measurements to be expected at the measurement points for the example of FIG. 1. Here curve 202 is the measured concentration at point A, and curve 204 is the measured concentration at point B. For example, when the plume location is at 102 (i.e., nearly centered on point A), the measured concentration at point A (i.e., curve 202 at time $t_1$) is higher than the measured concentration at point B (i.e., curve 204 at time $t_1$).

From these drawings, it is apparent that as the plume moves relative to measurement points A and B, the measured concentrations will tend to change in related ways. For example, if we assume that the plume moves horizontally from right to left between times $t_2$ and $t_3$, we expect the measured concentrations to move together (i.e., either both increasing or both decreasing), as shown on FIG. 2 between times $t_2$ and $t_3$.

However, the behavior is different if the plume moves vertically with respect to these measurement points. For example, if we assume that the plume moves vertically downward between times $t_4$ and $t_5$, we expect the measured concentrations to move opposite to each other (i.e., one increasing and the other decreasing), as shown on FIG. 2 between times $t_4$ and $t_5$. This example demonstrates that simple averaging of measured results can result in a significant loss of information (e.g., these informative correlations would disappear upon averaging the raw data).

An exemplary method for estimating the width w of a gas plume can include the following steps:

1) performing gas concentration measurements at two or more separated measurement points. Each data point is a simultaneous concentration measurement at the measurement points. This simultaneity can be provided in the raw data as first collected, or in later processing of the raw data (e.g., referral of sequentially collected data to a common time axis and interpolation to construct simultaneous multi-point concentration data points).

2) providing a time-independent gas plume model having at least w as a fitting parameter. The gas plume model also includes parameters for plume position.

3) fitting the gas plume model to the multi-location data points. The plume position is allowed to be a random variable to enable fitting to observed scatter in the data points. An estimate w* of the plume width is provided as an output.

Several features of this exemplary method are noteworthy. First, it is assumed that the data points are simultaneous multi-point measurements. If the multi-point data is acquired sequentially (as can often be convenient in practice), the raw data can be registered to a common time axis (e.g., by suitable interpolation methods) to provide the simultaneous multi-point measurements.

Second, for our purposes, a model is time-independent if it has no explicit dependence on time. However, time-independent models as defined herein can include time-dependent effects in an implicit manner. For example, the centroid of the plume in the measurement plane can vary in time (e.g., as shown on FIG. 1). The plume model includes the position of the center of the plume (e.g., transverse coordinate $y_0$ and $z_0$) as parameters. In reality, these coordinates are functions of time (i.e., $y_0(t)$ and $z_0(t)$). In the present work, this time dependence is handled by letting $y_0$ and $z_0$ be random variables in the fitting to the multi-point correlation data. This is in sharp contrast to conventional approaches that either 1) try to perform dynamical modeling explicitly relating to the time dependence of $y_0(t)$ and $z_0(t)$, e.g., by using measurements of atmospheric parameters such as stability class to predict the meander of the plume, or 2) try to eliminate this time dependence completely by averaging data prior to fitting the plume model. As another example, the plume width w can be modeled as a random variable. This amounts to implicitly accounting for a possible time dependence of plume width by allowing w to be a random variable in the model fitting. A benefit of this approach is that it naturally provides a variance associated with the reported width estimate w*, from which one can get an idea of how reliable the estimate w* is.

FIG. 3 shows a preferred arrangement of measurement points. Here measurement points A and B are vertically separated by a distance $d_z$ and measurement points A and C are horizontally separated by a distance $d_y$. Such an arrangement is preferred in practice because it can provide estimated widths $w_y$ and $w_z$ for both transverse dimensions of a gas plume. For example, the above-described method can be performed in two orthogonal directions. Here points A, B and C are in the same plane. Measurements relating to the two orthogonal directions can be performed either simultaneously or sequentially. If these measurements are performed sequentially, they can be put on a common time axis (e.g., by suitable interpolation methods) to provide simultaneous multi-points data. In this example, the data points can be triples $(C_A(t_i), C_B(t_i), C_C(t_i))$. Here $C_A$, $C_B$, and $C_C$ are measured concentrations at points A, B and C, and $t_i$ is a time index.

There are many possible analysis techniques for recovering the plume width from the multi-point correlation data. We describe one such method here, which uses a Markov-Chain Monte Carlo technique (in particular, a Metropolis-Hastings algorithm) to find an optimal set of plume characteristics, assuming a single peaked Gaussian distribution of concentration vs. transverse space, with different widths along the transverse horizontal and vertical axes y and z. The density of scatter points in the input 'A' vs. 'B' plane (or the input 'A'-'B'-'C' volume) is used as data to be optimized. Variables included in the Monte Carlo simulation are plume widths, plume centroid, and plume concentration peak height. Although costly in computing time, the advantage of this analysis technique is that it produces not only the nominal plume widths and peak heights that are needed to compute the emission rate, but also produces uncertainties for these quantities to be included in the overall uncertainty of the measurement.

Methods according to these principles have been tested in practice, and have performed well. In a first experiment, methane was released at a known rate of 500 sccm (standard cubic centimeters per minute). Three measurement points were located 21 m from the source arranged as in FIG. 3, with a vertical separation of 1.5 m and a horizontal separation of 1.8 m. FIG. 4 shows the measured wind speed for this experiment. FIG. 5 shows an exemplary correlation plot for two independent measurements at the same point 21 m from the source. FIG. 5 is included to show the level of noise in the data that is often encountered in practice. Ideally, the A-B correlation would be perfect because points A and B are co-located, but because of independent errors in the two measurements, a significant level of scatter is observed.

Figure 6A:
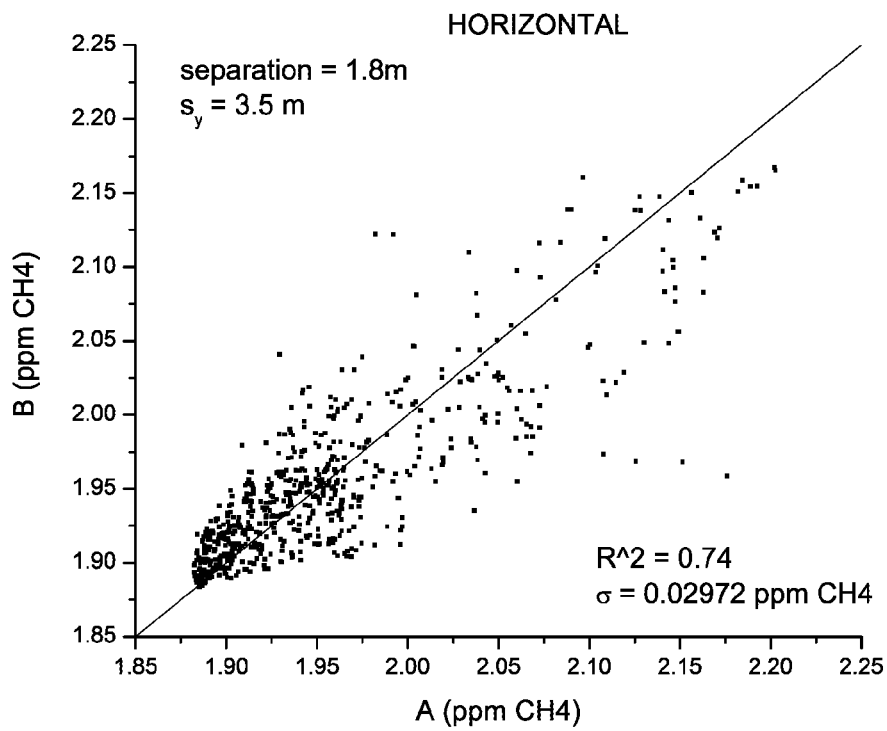
FIG. 6A shows an exemplary correlation plot for two measurement points separated horizontally by 1.8 m.
Figure 6B:
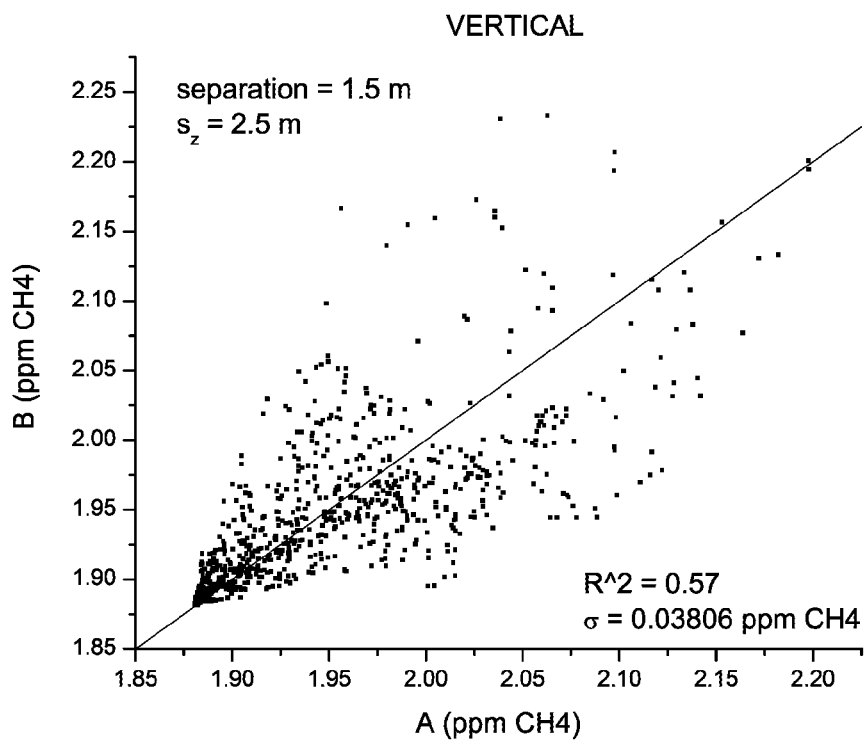
FIG. 6B shows an exemplary correlation plot for two measurement points separated vertically by 1.5 m.

FIG. 6A shows the correlation plot for the two measurement points separated horizontally by 1.8 m. FIG. 6B shows the correlation plot for the two measurement points separated vertically by 1.5 m. For both of these plots, it is apparent that the correlation is significantly less than that seen on FIG. 5, as a result of the separation of the measurement locations in FIGS. 6A-B. However, it is also the case that significant correlations remain, which are exploited in the present approach.

We fit these data to a Gaussian plume model $$C(x, y, z) = C_{peak} \exp\left[-\frac{(y-y_0)^2}{2w_y^2} - \frac{(z-z_0)^2}{2w_z^2}\right]$$

Here $y_0$ and $z_0$ are plume positions (random variables in the fitting). The total emissions Q* in this plume is the y-z surface integral of the product of C(y,z) and the surface normal wind speed V, for all y and positive z, which is approximately given by $$Q^* = x \, w_y w_z V C_{peak}$$

The average wind speed V is a measured value that is provided as an input to the fitting, and Q* is the estimated source emission rate. This fitting process gives widths $w_y$=3.5 m and $w_z$=2.5 m, a peak concentration of 0.22 ppm, and the average wind speed was 1.6 m/s. This gives an estimated plume emission Q* of 527 sccm, which compares well with the actual Q value of 650 sccm. It is noteworthy that the distance between the measurement points and the source does not need to be known (or even estimated) in order to obtain the source emission rate estimate Q*. The only atmospheric parameter used is average wind speed (measured perpendicular to the plane of the measurement points). No absolute wind direction measurements are needed. No estimates of atmospheric stability class or turbulent energy are needed.

Table 1 shows results from a second experiment. Here the first line is from the above described experiment, and the second line relates to a second experiment.

TABLE 1 results for source emission estimates

| $Q_{actual}$ (sccm) | distance (m) | $w^*_y$ (m) | $w^*_z$ (m) | $C_{peak}$ (ppm) | V (m/s) | Q* (sccm) |
|---|---|---|---|---|---|---|
| 650 | 21 | 3.5 ± 0.4 | 2.5 ± 0.5 | 0.22 | 1.6 | 527 |
| 3,400 | 49 | 4.9 ± 0.5 | 7.4 ± 0.7 | 0.17 | 3.0 | 3490 |

Here we see that good results are obtained, especially given the simplicity of the approach.

The measured correlations between separated measurement points are governed by the spatial extent of the plume along the axis connecting the two points relative to the distance between the two points. When the distance is much greater than the characteristic width of the plume, then the two input points will be completely uncorrelated. When the distance is much smaller than the characteristic width of the plume, then the points are well-correlated. Preferably the user can select the distance between the two points such that the inlet separation is the order of the width of the plume. In practice, unless the width of the plume is known beforehand, the user can select the distance between the two points such that the distribution of measurement points in the 'A'-'B' shows a significant yet not complete degree of correlation. Such a spacing between measurement points is preferred because it produces the most informative correlations for determining plume width parameters.

It is interesting to note, in the table above, that, in addition to an estimate of the source emission rate Q*, the method produces estimates of the plume widths, $w^*_y$ and $w^*_z$. These parameters are called the instantaneous plume width (i.e., the spatial width of a snapshot of the plume), as opposed to the time-averaged plume width, which includes both the instantaneous plume width and the meander of the plume centroid in time. For a point or near-point source of gas, and under atmospheric conditions where there is a mean non-zero advective wind, a plume of gas is formed which propagates downwind of the source. Diffusion in the atmosphere is such that the instantaneous transverse dimensions of the plume, approximated by $w^*_y$ and $w^*_z$, on average grow with increasing distance from the source. It is important to note that under typical conditions, as a given plume propagates downwind of a source, the plume grows larger and more diffuse with increasing distance from the source, in the same way that a smoke plume downwind of a campfire becomes larger and more diffuse with increasing distance. In other words, the instantaneous width of a plume is a monotonically increasing function of distance from the source; plumes do not get smaller and denser as they propagate away from a source. At a given distance from the source, under a given set of atmospheric conditions, the plume will diffuse to a certain spatial extent. However, this relationship can be reversed: for a given measurement of the spatial extent of the plume, and under a given set of conditions, the distance to the source can be estimated.

To determine the distance to the source, given the measurements of the spatial extent of the instantaneous plume, one must have a model for the rate of growth of the plume with distance. The rate of growth with distance is governed primarily by the overall magnitude of the advective wind and the degree of turbulence in the local atmosphere due to thermal gradients and due to local terrain and due to the flow of the wind over and around obstacles such as buildings or trees. Typically, under conditions of low advective wind and high turbulence, plumes are more diffuse at a given distance downwind of the source than they are under conditions of larger advective wind and low turbulence.

There are numerous atmospheric plume dispersion models provide a theoretical or empirical basis for determining the width of the instantaneous plume as a function of downwind distance from a point leak source. We describe one possible method for providing an estimate of the instantaneous plume widths. In a model proposed by Gifford in 1959 ("Statistical properties of a fluctuating plume dispersion model." Advances in geophysics 6 (1959): 117-137, hereby incorporated by reference in its entirety), the propagating plume is modeled as a Gaussian instantaneous plume convolved with a time dependent plume meander of the centroid of the plume. This model was extended by Pasquill and Turner (Workbook of atmospheric dispersion estimates: an introduction to dispersion modeling. CRC press, 1994, hereby incorporated by reference in its entirety) to provide estimates of the total plume widths (including the widths of the instantaneous plume and the contribution of plume meander). These Gaussian widths are tabulated as a function of the distance from the source to the receptor position along the mean direction of the wind, the stability class of the atmosphere, a quantity that depends upon solar irradiation, surface terrain and obstructions, and advective wind speed. Peterson and Lamb ("Comparison of results from a meandering-plume model with measured atmospheric tracer concentration fluctuations." Journal of Applied Meteorology 31.6 (1992): 553-564, hereby incorporated by reference in its entirety) provided a means for extending this model to estimate the instantaneous component of the plume width given the overall plume width (including meander) using the following simple linear expressions:

$$w^*_y = A(wPG_y) \text{ and } w^*_z = B(wPG_z)$$

where $wPG_y$ and $wPG_z$ are the widths as determined in the Pasquill-Gifford formalism and A and B are constants. In the Peterson and Lamb paper, A and B were experimentally determined to be about 0.22 and 0.38, respectively.

Note that $w^*_y$ and $w^*_z$ each provide estimates of the distance X* to the emission source. There are several options for how to combine the two estimates. Two examples are providing the mean of the two distance estimates to the user, and by providing both estimates as a range to the user.

Other plume propagation models that do provide a mapping of instantaneous plume width from propagation distance can also be employed to estimate the distance from the source given the instantaneous plume width estimates. In addition, plume models that provide estimates of the instantaneous plume width with propagation time can be used to estimate total propagation time from the source given the measured instantaneous widths. Local measurements of the advective wind at the location of the measurements can then be used to estimate the distance from the source given the propagation time. Estimates of the advective wind can also be obtained from nearby (<5 km) weather stations, or from weather models.

Note that estimates of atmospheric turbulence can be provided by measurements of direct atmospheric quantities (such as from fast (>1 Hz) 3-dimensional measurements of local winds) or measurements of indirect quantities such as solar irradiation, surface albedo, surface cover, or characterization of local terrain and obstructions. These measurements can provide direct input into the atmospheric model that determines the relationship between plume width and distance, thus improving the estimates of distance to the source.

Figure 7:
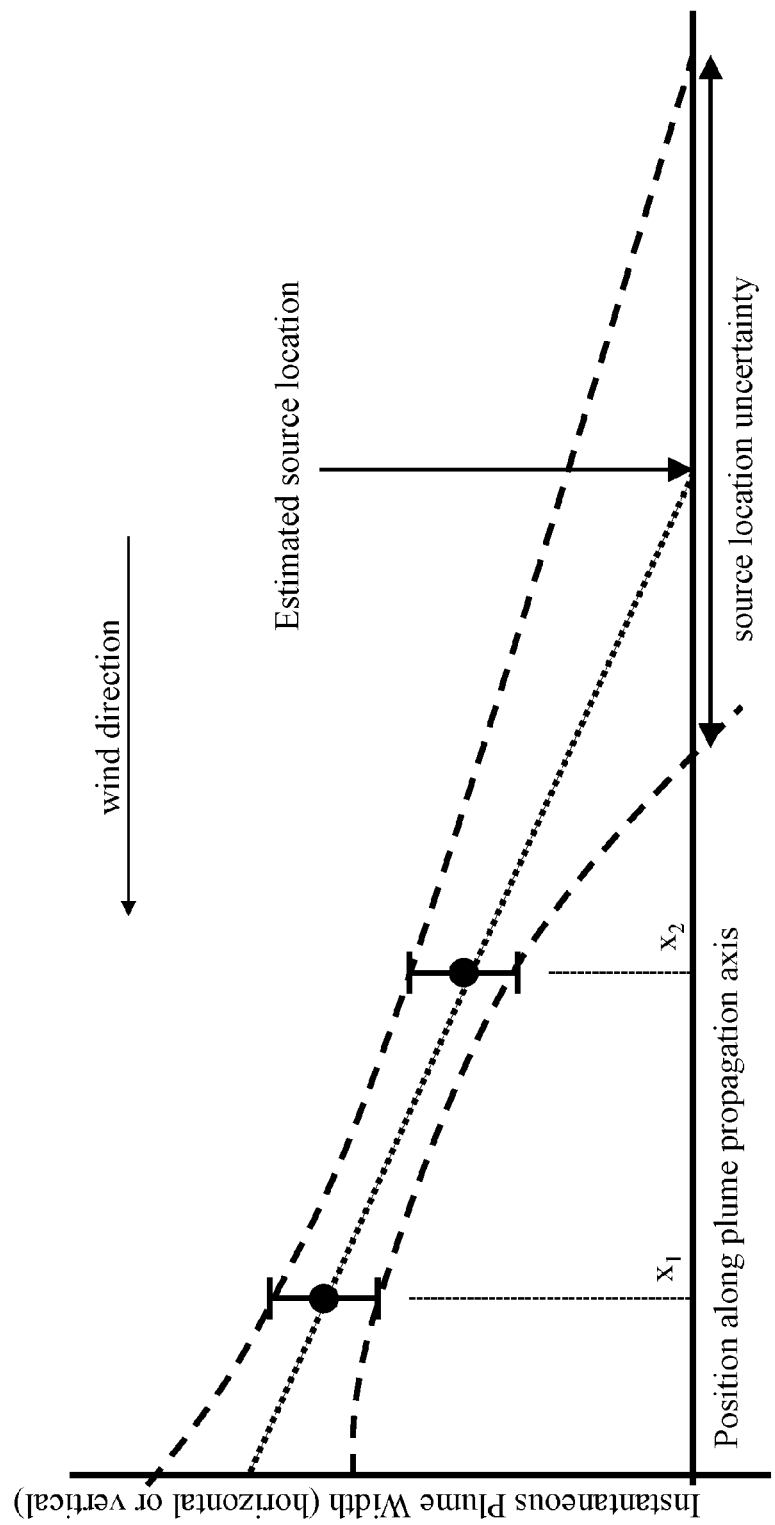
FIG. 7 shows distance estimation using two estimates of plume width combined with an assumed functional form for X*(w*).

Thus far, we have considered the problem of estimating the distance to a source from a measurement of the instantaneous plume width at a single downwind location, given an atmospheric model. Now we consider the possibility of making measurements of the instantaneous plume width at two or more locations along the plume propagation path. With two or more locations, one can obtain an estimate of the change in size of the plume from one location to the next. By looking at the change in the plume width, one may estimate the distance to the source by comparing the relative change in the width. FIG. 7 illustrates this situation. In this example, two measurements of the instantaneous plume width are made at two locations ($x_1$ and $x_2$). From these two measurements, and an estimate of the functional form for the growth of the plume width with distance (in this case linear), an estimate of the distance to the source can be provided. Note that the growth rate of the plume (i.e., the slope of the line used to estimate the source location) does not need to be provided by a model. Only the functional form (i.e., linear) is required. Other functional forms can be used. For example, a square root dependence of the plume width on propagation distance can be used. Alternatively, the power law dependences provided in the Pasquil-Gifford formalism can be used.

One such application of these techniques is in the field of finding natural gas leaks from natural gas distribution infrastructure, such as buried pipelines or customer meters or other such facilities. In this application, for example, a concentration detector can be used to detect the presence of natural gas (e.g., by detecting methane). Detecting the presence of an elevated level of methane may indicate the presence of a natural gas leak somewhere upwind of the detection location, but without a distance estimate to the source, one would have to slowly walk upwind until the source of the leak is found by looking for highly elevated concentrations right at the source of the leak. In contrast, by using the methodology above to quantify the instantaneous plume width and thus determine the distance to the source, one can jump directly to the expected location of the leak and search for the source there, leading to a much faster search protocol.

The invention claimed is:

1. A method for estimating a distance to a source of a gas leak from an estimate of a width w of a gas plume from the gas leak, the method comprising:

performing multiple gas concentration measurements at two or more separated measurement points, wherein each data point of the gas concentration measurements is a simultaneous concentration measurement at the measurement points;

providing a time-independent gas plume model having at least plume spatial width w as a fitting parameter, wherein the gas plume model also includes parameters for plume position;

fitting the gas plume model to the data points, wherein the plume position is allowed to be a random variable to enable fitting to observed scatter in the data points, to obtain an estimate w* of the plume spatial width w; and providing as an output an estimate of a distance X* between the measurement points and a source of the gas plume from the estimate of the plume spatial width w*.

2. The method of claim 1, wherein the distance X* depends in a monotonically increasing manner on w*.

3. The method of claim 2, wherein a relationship between X* and w* is derived from an atmospheric plume dispersion model.

4. The method of claim 3, wherein the atmospheric plume dispersion model is a Gaussian plume model.

5. The method of claim 3, where the atmospheric plume dispersion model incorporates one or more parameters selected from the group consisting of: wind speed, atmospheric turbulence, solar irradiance, local terrain, surface albedo, surface cover, and nearby wind obstructions.

6. The method of claim 2, wherein the distance estimate X* is determined from two estimates of w* made at two distinct locations along the path of the propagation of the plume, combined with an assumed functional form for the monotonically increasing function relating w* and X*.

7. The method of claim 6, wherein the functional form is linear.

8. The method of claim 6, wherein the functional form is determined from a plume propagation model.

9. The method of claim 6, wherein the functional form is determined empirically from experimental data.

10. A method for estimating a distance to a source of a gas leak, the method comprising:

performing the method of claim 1 in two orthogonal directions y and z;

wherein all measurement points are in a common measurement plane;

wherein the distance estimate X* depends on both $w^*_y$ and $w^*_z$.

11. The method of claim 10, wherein the measurement points include three points having y-z coordinates (0,0), ($d_y$,0), (0, $d_z$).

12. The method of claim 10, wherein measurements relating to the two orthogonal directions are performed simultaneously.

13. The method of claim 10, wherein measurements relating to the two orthogonal directions are performed sequentially and then registered to a common time axis to provide the simultaneous concentration measurements at the measurement points.

* * * * *